(12) United States Patent
Hasegawa et al.

(10) Patent No.: US 6,451,372 B2
(45) Date of Patent: Sep. 17, 2002

(54) BIOSENSOR AND METHOD OF PRODUCING THE SAME

(75) Inventors: Miwa Hasegawa, Nara; Tomohiro Yamamoto, Hirakata; Motokazu Watanabe; Shin Ikeda, both of Katano; Shiro Nankai, Hirakata, all of (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/770,946

(22) Filed: Jan. 26, 2001

(30) Foreign Application Priority Data

Jan. 27, 2000 (JP) ........................ 2000-018834

(51) Int. Cl.⁷ .................... B05D 3/00; G01N 27/327
(52) U.S. Cl. ................... 427/2.13; 204/403.14
(58) Field of Search ............... 204/403, 403.1, 204/403.14; 427/2.13

(56) References Cited

U.S. PATENT DOCUMENTS 5,609,749 A * 3/1997 Yamauchi et al. ....... 205/777.5
5,730,124 A * 3/1998 Yamauchi .................. 128/630

FOREIGN PATENT DOCUMENTS

JP        A-2-062952        3/1990

OTHER PUBLICATIONS

R. Foster, J. Cassidy and Eilish O'Donoghue, Electrochemical Diagnostic Strip Device for Total Cholesterol and Its Subfractions, *Electroanalysis 2000*, vol. 12, No. 9, pp. 716–721 (2000).

* cited by examiner

*Primary Examiner*—T. Tung
*Assistant Examiner*—Alex Noguerola
(74) *Attorney, Agent, or Firm*—Akin, Gump, Strauss, Hauer & Feld, L.L.P.

(57) ABSTRACT

The present invention provides a biosensor that has a reaction reagent system easily dissolved even in a sample solution containing a high concentration of a substrate and ensures rapid and highly accurate measurement. The method of forming a target reaction layer according to the present invention dissolves a material constituting the target reaction layer in a solvent of a sublimable substance to prepare a solution, applies the solution in a desired area to form the target reaction layer, freezes the applied solution, and sublimates the solvent included in a solid matter of the frozen solution under reduced pressure for removal. The resultant reaction layer has a large surface area and is easily dissolved in the sample solution to enable rapid measurement.

15 Claims, 4 Drawing Sheets

BIOSENSOR AND METHOD OF PRODUCING THE SAME

BACKGROUND OF THE INVENTION

The present invention relates to a biosensor that ensures rapid and highly accurate quantification of a specific component contained in a sample by a simplified procedure, and more specifically to a method of forming a reaction layer of the biosensor.

One proposed biosensor adopts the simple technique that quantifies a specific component in a sample without diluting or stirring a sample solution (Japanese Laid-Open Patent Publication No. Hei 2-062952).

This prior art biosensor is manufactured by forming an electrode system, which includes a measuring electrode, a counter electrode, and a reference electrode, on an electrically insulating base plate by a known method like screen printing and further forming an enzyme reaction layer, which includes a hydrophilic polymer, an oxidoreductase, and an electron mediator, on the electrode system. A buffer may be added to the enzyme reaction layer according to the requirements.

When a sample solution including a substrate is dropped on the enzyme reaction layer of the biosensor manufactured in the above manner, the enzyme reaction layer is dissolved to make the enzyme react with the substrate and reduce the electron mediator. After completion of the enzyme reaction, the concentration of the substrate included in the sample solution is determined, based on the observed oxidation current flowing in the process of electrochemically oxidizing the reduced electron mediator.

The following describes a glucose sensor as one example of the biosensor.

A generally known method of quantifying glucose combines glucose oxidase with either an oxygen electrode or a hydrogen peroxide electrode.

Glucose oxidase selectively oxidizes a substrate β-D-glucose to D-glucono-δ-lactone with oxygen as the electron mediator. In the course of this reaction, oxygen is reduced to hydrogen peroxide. Glucose is quantified by measuring the quantity of oxygen consumption due to the reduction with the oxygen electrode or by measuring the quantity of hydrogen peroxide production with the hydrogen peroxide electrode, such as a platinum electrode.

The quantification of some substrates of interest according to this prior art method is, however, significantly affected by the concentration of dissolved oxygen. The measurement is unavailable in the absence of oxygen. Another type of the glucose sensor has accordingly be developed, which does not use oxygen as the electron mediator but utilizes a metal complex or an organic compound, such as potassium ferricyanide, a ferrocene derivative, or a quinone derivative, for the electron mediator.

The glucose sensor of this type oxidizes the reduced form electron mediator, which results from the enzyme reaction, on an electrode and determines the concentration of glucose from the observed oxidation current.

The biosensor according to this technique is, in principle, applicable to measurement of various substances by using an enzyme that acts upon each substance of interest as the substrate.

For example, application of cholesterol oxidase or cholesterol dehydrogenase and cholesterol esterase for the oxidoreductase enables measurement of serum cholesterol, which is used as a diagnostic indication in a diversity of medical institutes.

The progress of the enzyme reaction of cholesterol esterase is remarkably slow. Addition of an appropriate surface active agent enhances the activity of cholesterol esterase and shortens the time required for the whole reaction.

In this prior art biosensor, for example, a reaction layer is obtained by dissolving potassium ferricyanide, which is one of the electron mediators discussed above, alone or with other components in a solvent, dropping the solution in a desired area for the reaction layer on a base plate, and drying the dropped solution with warm blast. In this reaction layer, potassium ferricyanide deposits in the form of needles having the longitudinal dimension of even greater than 1 mm. The reaction layer accordingly has the heterogeneous configuration, which worsens the measurement accuracy of a resultant sensor.

Compared with that in the glucose sensor, the reaction layer in the cholesterol sensor contains a higher concentration of the corresponding enzyme. The prior art method that forms such a reaction layer by drying the dropped solution with warm blast causes the resultant reaction layer to be slowly dissolved in a sample solution and have poor response.

BRIEF SUMMARY OF THE INVENTION

The object of the present invention is thus to provide a biosensor that has high accuracy and excellent response to a substrate even in a high concentration range of the substrate.

In order to form a reaction layer containing a reagent such as potassium ferricyanide, which tends to deposit from an aqueous solution in the form of crystals, or a high concentration of an enzyme, the inventors have found the suitable method that dissolves a material constituting a target reaction layer in a solvent of a sublimable substance to prepare a solution, applies the solution in a desired area to form the target reaction layer, freezes the applied solution, and sublimates the solvent included in a solid matter of the frozen solution under reduced pressure for removal. This method gives the reaction layer that has a large surface area and is easily dissolved i n a sample solution. The technique of the present invention is based on these findings.

At least part of the a above and the other related objects of the present invention is attained by a method of manufacturing a biosensor, which includes an electrically insulating base plate, an electrode system that is provided on the electric ally insulating base plate and includes a measuring electrode and a counter electrode, and a reaction reagent system that includes at least an oxidoreductase and an electron mediator as reagents. The reagents of the reaction reagent system are present as a reaction layer structure that includes at least one reaction layer and is formed on or in the vicinity of the electrode system . The method includes the step of forming a specific reaction layer of the reaction layer structure that contains at least one specific reagent of the reaction reagent system. The step comprises:

(1) dissolving the at least one specific re agent in a solvent of a sublimable substance to prepare a solution;

(2) applying the solution in a desired area to form the specific reaction layer;

(3) freezing the applied solution; and (4) sublimating the solvent included in a solid matter of the frozen solution under reduced pressure for removal.

In accordance with one preferable application of the present invention, the specific reaction layer contains all the reagents of the reaction reagent system.

In accordance with another preferable application of the present invention, the reaction layer structure has a plurality of reaction layers and only the specific reaction layer contains the at least one specific reagent of the reaction reagent system.

In accordance with still another preferable application of the present invention, the method includes the step of forming a stack of plural reaction layers as the reaction layer structure, wherein the at least one specific reagent of the reaction reagent system is contained only in an upper-most reaction layer of the stack. The step includes the sub-steps of: pre-forming the stack of plural reaction layers except the upper-most reaction layer; dissolving the at least one specific reagent in a solvent of a sublimable substance to prepare a solution and applying the solution on the pre-formed stack of plural reaction layers without the upper-most reaction layer; freezing the applied solution; and sublimating the solvent included in a solid matter of the frozen solution under reduced pressure for removal.

It is preferable that the method further includes the steps of: forming a cover member on the electrically insulating base plate, which is joined with the base plate to define a sample solution supply pathway, through which a sample solution flows to the electrode system; causing the reaction layer structure to be exposed to the sample solution supply pathway; and forming at least one reaction layer of the reaction layer structure on the cover member.

In the case where the oxidoreductase is an enzyme functioning as a catalyst of the oxidation reaction of cholesterol, it is preferable that the electron mediator is included in another reaction layer different from a reaction layer containing the enzyme.

In accordance with another preferable application of the present invention, the oxidoreductase is an enzyme functioning as a catalyst of the oxidation reaction of cholesterol, and the electron mediator is contained in another reaction layer different from a reaction layer containing the enzyme.

In accordance with still another preferable application of the present invention, the oxidoreductase is an enzyme functioning as a catalyst of the oxidation reaction of cholesterol, and the layer containing the enzyme further contains a surface active agent.

In accordance with one preferable application of the present invention, the above-mentioned at least one specific reagent of the reaction reagent system is an oxidoreductase or potassium ferricyanide which is an electron mediator.

It is also preferable that at least lower-most reaction layer of the reaction layer structure includes a hydrophilic polymer.

While the novel features of the invention are set forth particularly in the appended claims, the invention, both as to organization and content, will be better understood and appreciated, along with other objects and features thereof, from the following detailed description taken in conjunction with the drawings.

DETAILED DESCRIPTION OF THE INVENTION

Figure 1:
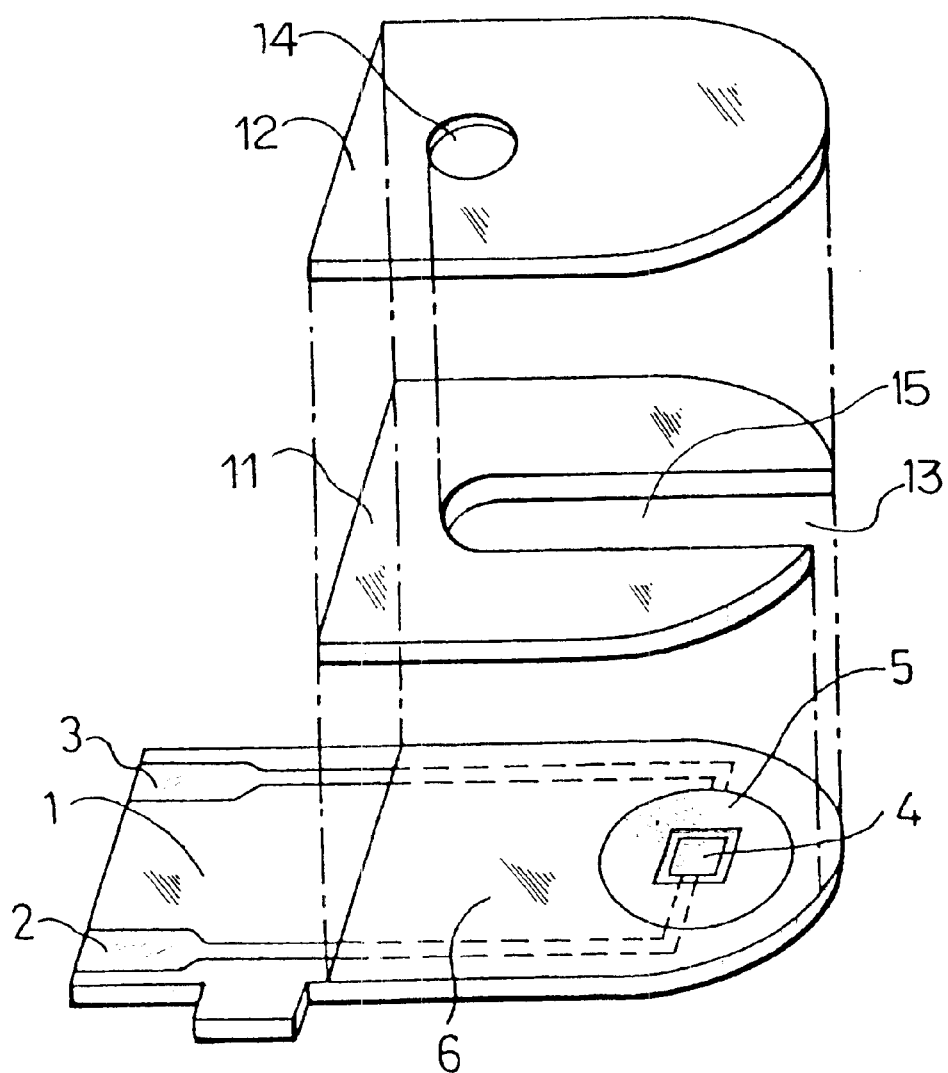
FIG. 1 is a disassembled perspective view illustrating the structure of a biosensor without a reaction layer structure in one embodiment of the present invention.

One aspect of the present invention is a method of manufacturing a biosensor which comprises an electrically insulating base plate, an electrode system including a measuring electrode and a counter electrode formed on the base plate, and a reaction reagent system including at least an oxidoreductase and an electron mediator, wherein reagents of the reaction reagent system are included in one or more reaction layers formed on or in the vicinity of the electrode system. This method includes the step of forming the one or more reaction layers and the step comprises:

dissolving the reagents in a solvent of a sublimable substance to prepare a solution; applying the solution in a desired area to form the one or more reaction layers; freezing the applied solution; and sublimating the solvent included in a solid matter of the frozen solution under reduced pressure for removal.

Another aspect of the present invention is a method of manufacturing a biosensor which comprises an electrically insulating base plate, an electrode system including a measuring electrode and a counter electrode formed on the base plate, and a reaction reagent system including at least an oxidoreductase and an electron mediator, wherein reagents of the reaction reagent system are included in a plurality of reaction layers formed on or in the vicinity of the electrode system, and only a specific reaction layer of the plurality of reaction layers contains at least one specific reagent of the reaction reagent system. The method includes the step of forming the specific reaction layer, and the step comprises: dissolving the at least one specific reagent in a solvent of a sublimable substance to prepare a solution; applying the solution in a desired area to form the reaction layer; freezing the applied solution; and sublimating the solvent included in a solid matter of the frozen solution under reduced pressure for removal.

A further aspect of the present invention is a method of manufacturing a biosensor which comprises an electrically insulating base plate, an electrode system including a measuring electrode and a counter electrode formed on the base plate, and a reaction reagent system including at least an oxidoreductase and an electron mediator, wherein reagents of the reaction reagent system are included in one or more reaction layers formed on or in the vicinity of the electrode system, and at least one specific reagent of the reaction reagent system is contained only in an upper-most layer of a specific reaction layer comprising a stack of layers. The method includes the step of forming the specific reaction layer and the step comprises: pre-forming the stack of layers except the upper-most layer; dissolving the at least one specific reagent in a solvent of a sublimable substance to prepare a solution; applying the solution on the pre-formed stack of layers without the upper-most layer; freezing the applied solution; and sublimating the solvent included in a solid matter of the frozen solution under reduced pressure for removal.

As described above, the method of the present invention forms a specific reaction layer or an upper-most reaction layer in a stack of plural reaction layers, which contains at least one specific reagent, by dissolving a material constituting the reaction layer including the specific reagent in a solvent of a sublimable substance to prepare a solution, applying the solution in a desired area to form the reaction layer, freezing the applied solution, and sublimating the solvent included in a solid matter of the frozen solution under reduced pressure for removal. This method gives the reaction layer having a porous structure that is composed of substantially uniform fine particles and has a large surface area. This arrangement enhances the solubility of the reaction layer in a sample solution and shortens the time required for measurement. This technique is especially effective in the case where the sample solution has a high concentration of a substrate. The high concentration of the substrate in the sample solution results in a high viscosity of the sample solution, so that the prior art reaction layer is not easily dissolved. The arrangement of the present invention enhances the solubility of the reaction layer even in the sample solution having the high concentration of the substrate.

This method is especially effective for the electron mediator among the various reagents of the reaction reagent system. The electron mediator may be potassium ferricyanide or a suitable redox compound selected among a variety of redox compounds having the electron transferring ability to and from an oxidoreductase like cholesterol oxidase. It is preferable that the electron mediator alone is carried on the biosensor, in order to increase the surface area of the electron mediator and enhance the solubility thereof.

The solvent of the sublimable substance preferably used in the present invention is either electrochemically inactive or oxidant and accordingly does not reduce nor modify the electron mediator or the enzyme. Water is the best solvent for this purpose. Dimethylformamide, dimethyl sulfoxide, and quinones like para-benzoquinone are also available for the solvent of the electron mediator. Water or a buffer is preferable for the solvent of the enzyme. Other applicable solvents include about 40% aqueous solution of dimethylformamide and about 20% aqueous solution of ethanol.

The oxidoreductase used in the present invention is an enzyme for a measuring subject as a substrate. Thus, glucose oxidase is used in the glucose sensor. In order to measure serum cholesterol concentrations as the diagnostic standard, cholesterol oxidase or cholesterol dehydrogenase as the enzyme functioning as a catalyst of the oxidation reaction of cholesterol, and cholesterol esterase as the enzyme functioning as a catalyst of the process of converting cholesterol ester into cholesterol are used. Since the enzyme reaction of cholesterol esterase proceeds very slowly, an addition of an appropriate surface active agent improves the activity of cholesterol esterase, enabling reduction of the time which is necessary for the whole reaction.

A cholesterol sensor according to the present invention has a reaction layer structure that may include a plurality of reaction layers, that is, a layer containing a hydrophilic polymer, a layer containing an enzyme that functions as a catalyst of the oxidation reaction of cholesterol, a layer containing a surface active agent, a layer containing cholesterol esterase, and a layer containing the electron mediator. The surface active agent, the enzyme functioning as the catalyst of the oxidation reaction of cholesterol, and cholesterol esterase may be included in one mixed reaction layer. The reaction layers arranged at a plurality of different positions may be formed as divisions of an identical composition or may alternatively have different compositions. These reaction layers are arranged on or in the vicinity of the electrode system in the biosensor.

The biosensor may have a cover member that is joined with the base plate with the electrode system formed thereon to define a sample solution supply pathway, through which a sample solution flows to the electrode system. In this case, the reaction layer may be formed at a specific position exposed to the sample solution supply pathway or at an opening of the sample solution supply pathway. The reaction layer may be formed at any suitable positions as long as the reaction layer is easily dissolved in a supply of the sample solution and reaches the electrode system. A hydrophilic polymer layer is preferably formed on the electrode system to protect the electrode system and prevent the reaction layer from being peeled off. It is also preferable that a hydrophilic polymer layer is formed as the base of the reaction layer or that a hydrophilic polymer is included in a lower-most reaction layer.

It is preferable that the reaction layer containing the electron mediator is separate from the surface active agent for the enhanced solubility, and is also separate from the enzyme functioning as the catalyst of the oxidation reaction of cholesterol, e.g. cholesterol esterase for the enhanced storage stability.

In some biosensors for measuring the blood sugar (see, for example, Japanese Laid-Open Patent Publication No. Hei 2-062952), a lipid-containing layer is formed to cover the layer formed on the electrode system, in order to facilitate introduction of the sample solution into the reaction layer. The biosensor of the present invention for measuring cholesterol includes the surface active agent, which has the similar functions to those of the lipid, and accordingly does not require the lipid layer.

Examples of the hydrophilic polymer include water-soluble cellulose derivatives, especially ethyl cellulose, hydroxypropyl cellulose, carboxymethyl cellulose, polyvinyl pyrrolidone, polyvinyl alcohol, gelatin, polyacrylic acid and salts thereof, starch and derivatives thereof, polymer of maleic anhydride and salts thereof, polyacrylamide, methacrylate resin, poly-2-hydroxyethyl methacrylate and the like.

As the surface active agent, it is possible to use an arbitrary choice of n-octyl-β-D-thioglucoside, polyethylene glycol monodddecyl ether, sodium cholate, dodecyl-β-maltoside, sucrose monolaurate, sodium deoxycholate, sodium taurodeoxycholate, N,N-bis(3-D-gluconeamidopropyl)deoxycholeamide and polyoxyethylene(10) octyl phenyl ether.

When a lipid is used, an amphipathic phospholipid such as lecithin, phosphatidyl choline and phosphatidyl ethanolamine is preferably used.

As the measuring method of the oxidation current, a two-electrode system composed only of a measuring electrode and a counter electrode and a three-electrode system further comprising a reference electrode are applicable, and the three-electrode system can give more accurate measurement results.

The present invention is described in detail by referring to preferred embodiments.

FIG. 1 is a disassembled perspective view illustrating a biosensor without a reaction layer in a first embodiment of the present invention.

Silver paste is printed on an electrically insulating base plate 1 of polyethylene terephthalate by the technique of screen printing to form leads 2 and 3. Electrically conductive carbon paste including a resin binder is further printed on the base plate 1 to form an electrode system including a measuring electrode 4 and a counter electrode 5. Electrically insulating paste is also printed on the base plate 1 to form an electrically insulating layer 6. The electrically insulating layer 6 partly covers the leads 2 and 3 and keeps an exposed area of the measuring electrode 4 and the counter electrode 5 fixed.

A cover 12 with an air vent 14 and a spacer 11 are bonded to the electrically insulating base plate 1 according to the positional relationship shown by the dashed line in FIG. 1.

This completed a cholesterol sensor. The spacer 11 has a slit 15, which is joined with the base plate 1 and the cover 12 to define a sample solution supply pathway. The sample solution supply pathway has an opening 13.

Figure 2:
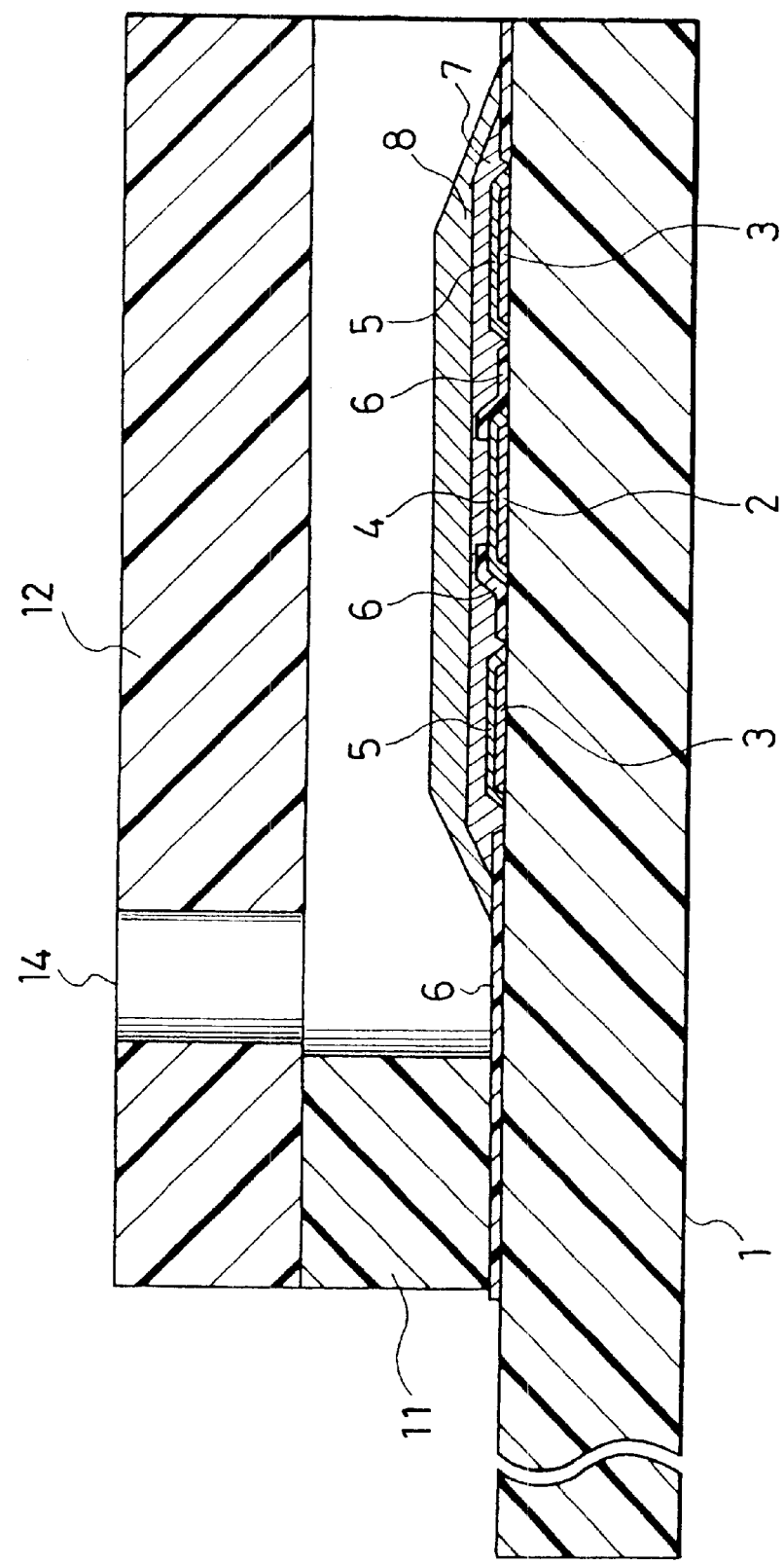
FIG. 2 is a vertical sectional view illustrating a main part of the biosensor shown in FIG. 1.

FIG. 2 is a vertical sectional view illustrating the biosensor of the first embodiment. A hydrophilic polymer layer 7 is formed on the electrode system upon the electrically insulating base plate 1. The hydrophilic polymer layer 7 is obtained by dropping an aqueous solution of a hydrophilic polymer and drying the dropped solution with warm blast. A reaction layer 8 including reaction reagents is formed on the hydrophilic polymer layer 7. In the case of a cholesterol sensor, the reaction layer 8 includes cholesterol oxidase, cholesterol esterase, the surface active agent, and the electron mediator. The reaction layer 8 is prepared by dropping an aqueous solution of such reagents on the hydrophilic polymer layer 7, freezing the dropped solution, and drying the frozen solution under reduced pressure for sublimation of the water content.

Figure 3:
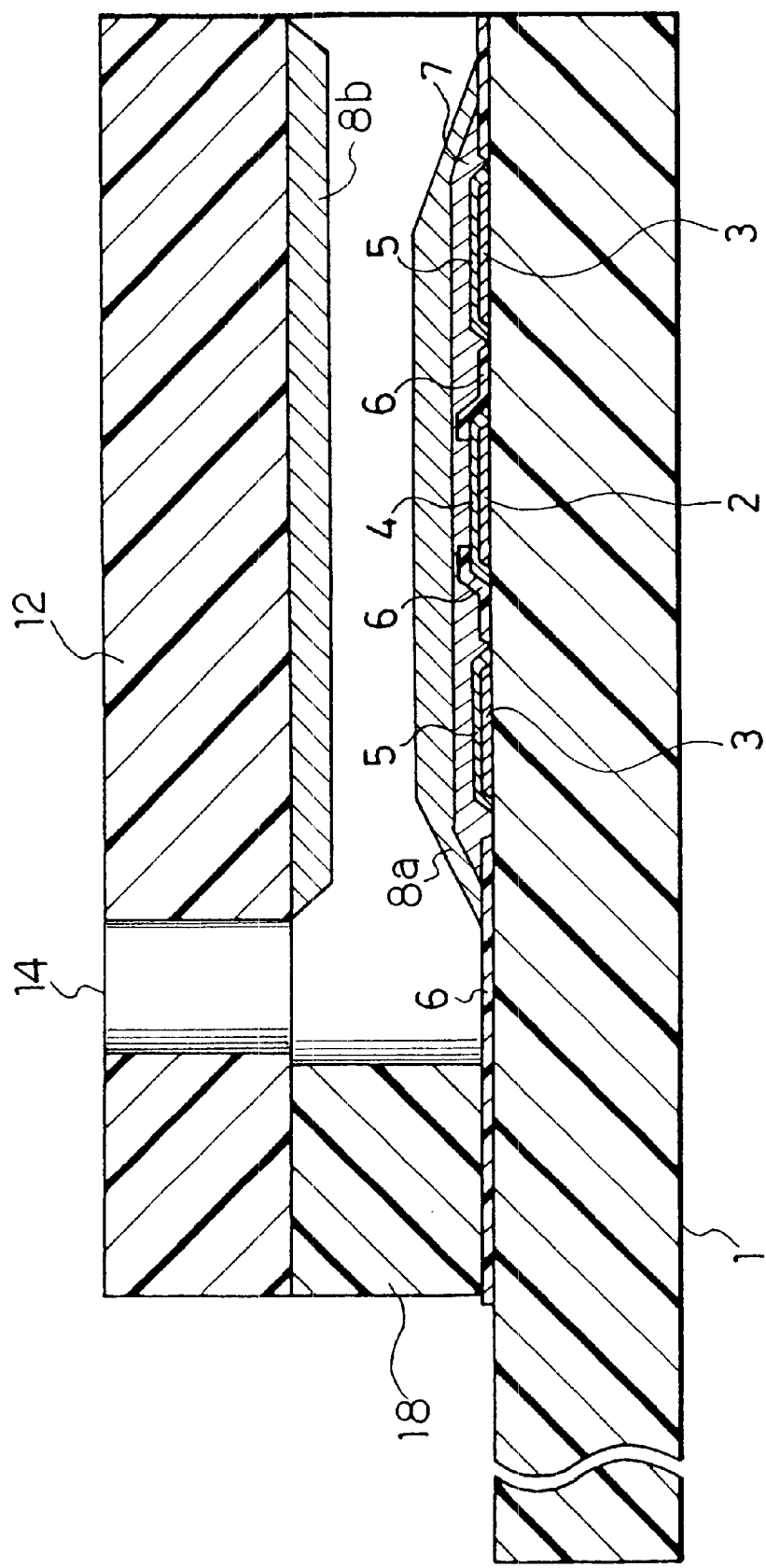
FIG. 3 is a vertical sectional view illustrating a main part of another biosensor in another embodiment of the present invention.

FIG. 3 is a vertical sectional view illustrating another biosensor in a second embodiment of the present invention. Like the first embodiment, the hydrophilic polymer layer 7 is formed on the electrode system upon the electrically insulating base plate 1. In the second embodiment, reaction layers 8a and 8b are formed respectively on the hydrophilic polymer layer 7 and on the surface of the cover 12 that is exposed to the sample solution supply pathway. Each of these reaction layers 8a and 8b is prepared by dropping an aqueous solution including the constituents of each layer at a specified position, freezing the dropped solution, and drying the frozen solution under reduced pressure for sublimation of the water content.

In accordance with one embodiment of the cholesterol sensor, the reaction layer 8a includes cholesterol oxidase, cholesterol esterase, and the surface active agent, whereas the reaction layer 8b includes the electron mediator. In accordance with another embodiment, the reaction layer 8a includes cholesterol oxidase and cholesterol esterase, whereas the reaction layer 8b includes the surface active agent and the electron mediator.

In accordance with still another embodiment, any one of the reaction layers 8, 8a, and 8b is constructed as a stack of plural reaction layers. At least an upper-most layer of the stack is prepared through the steps of freezing an aqueous solution of at least one reagent to be contained in the upper-most layer and removing the water content by sublimation. The at least one reagent included in the upper-most layer is, for example, potassium ferricyanide, which forms coarse crystals when the aqueous solution is dried with warm blast. It is preferable that the reaction layer 8b includes a hydrophilic polymer or is formed on a hydrophilic polymer layer. This arrangement effectively prevents the reaction layer 8b from being peeled off.

Example 1

Example 1 is a cholesterol sensor having the structure of FIG. 3, wherein the reaction layer 8a includes the electron mediator and the reaction layer 8b includes cholesterol oxidase, cholesterol esterase, and the surface active agent. This cholesterol sensor was prepared in the following manner.

The procedure of Example 1 first prepared a 0.5% by weight of aqueous solution containing sodium carboxymethyl cellulose (hereinafter referred to as CMC), dropped 5 μl of the aqueous solution on the electrode system upon the base plate 1, and dried the dropped solution in a drying apparatus with warm blast of 50° C. for 10 minutes. This gave the CMC layer 7. The procedure then dissolved potassium ferricyanide in water to prepare a 1 M aqueous solution, dropped 1 μl of the aqueous solution on the CMC layer 7, and dried the dropped solution in the drying apparatus with warm blast of 50° C. for 10 minutes. This gave the reaction layer 8a including potassium ferricyanide.

The procedure, on the other hand, prepared a mixed aqueous solution by dissolving cholesterol oxidase coming from Nocardia (EC.1.1.3.6, hereinafter referred to as ChOD) and cholesterol esterase coming from Pseudomonas (EC.3.1.1.13, hereinafter referred to as ChE) in water and adding polyoxyethylene(10)octyl phenyl ether (TritonX-100) as a surface active agent. The procedure then dropped 2.5 μl of the mixed aqueous solution in the recess defined by the slit 15 of the cover member including the cover 12 and the spacer 11, froze the dropped solution with liquid nitrogen of −196° C., and dried the frozen solution in a Kjeldahl flask set in a freeze-drying apparatus for 3 hours. This gave the reaction layer 8b including 4 units (U) of cholesterol oxidase, 10 U of cholesterol esterase, and 3% by weight of the surface active agent. The reaction layer 8b held the contour formed immediately after dropping 2.5 μl of the mixed aqueous solution and had the porous structure having an extremely large surface area.

The cholesterol sensor was completed by bonding the cover member to the base plate.

Figure 4:
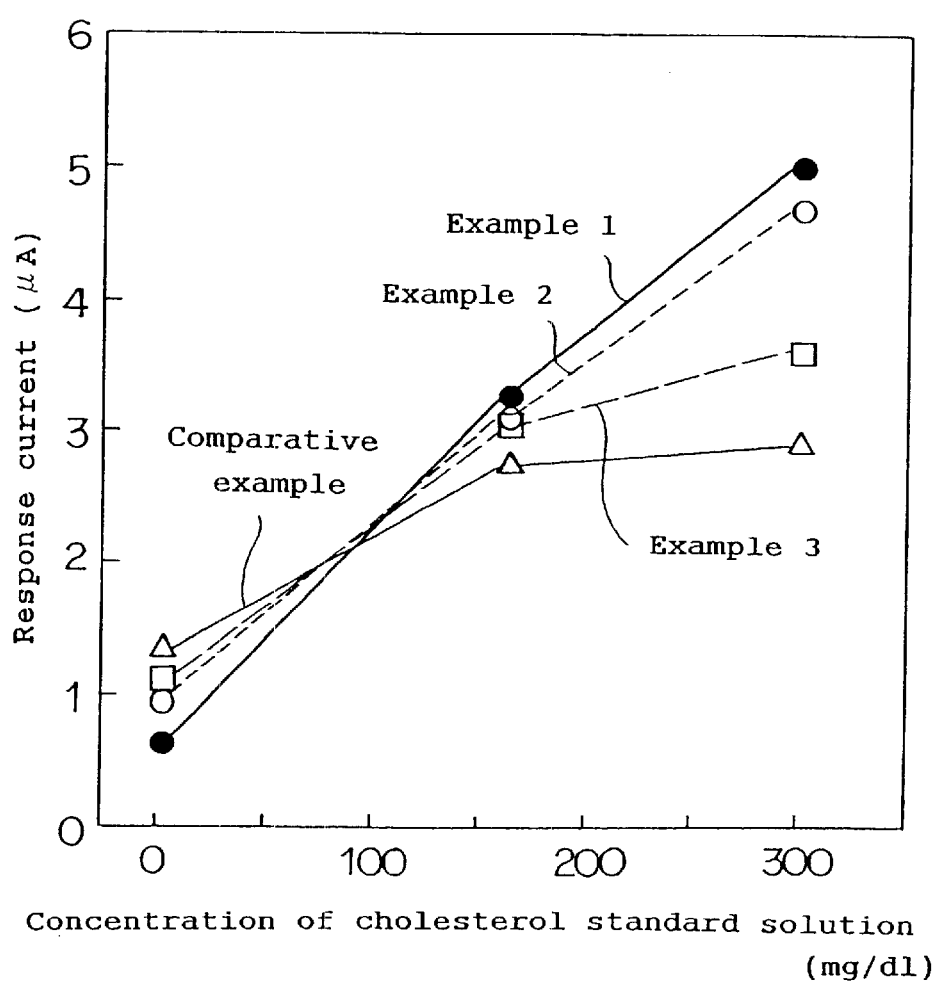
FIG. 4 is a graph showing responses of cholesterol sensors prepared as examples of the present invention and comparative examples.

The procedure supplied 1 μl of a cholesterol standard solution containing cholesterol and cholesterol linoleate, which is one of the cholesterol esters, through the opening 13 of the sample solution supply pathway to the cholesterol sensor thus prepared, applied a pulse voltage of +0.5 V toward the anode on the measuring electrode relative to the counter electrode as the reference 3 minutes after the supply, and measured the electric current 5 seconds after the application. The results are shown in the graph of FIG. 4.

Example 2

Example 2 is a cholesterol sensor having the structure of FIG. 3, wherein the reaction layer 8a includes the electron mediator and the reaction layer 8b includes cholesterol oxidase, cholesterol esterase, the surface active agent, and 0.125% by weight of CMC. This cholesterol sensor was prepared in the following manner.

The CMC layer 7 was formed on the electrode system upon the electrically insulating base plate 1 in the same manner as discussed in Example 1. The procedure of Example 2 dissolved potassium ferricyanide in water to prepare an aqueous solution, dropped 1 μl of the aqueous solution on the CMC layer 7, and dried the dropped solution in the drying apparatus with warm blast of 50° C. for 10 minutes. This gave the reaction layer 8a including potassium ferricyanide. The procedure. on the other hand, prepared a mixed aqueous solution by dissolving ChOD, ChE, the surface active agent, and CMC in water, dropped 2.5 μl of the mixed aqueous solution in the recess defined by the slit 15 of the cover member including the cover and the spacer, froze the dropped solution with liquid nitrogen, and dried the frozen solution in a Kjeldahl flask set in the freeze-drying apparatus for 3 hours. This gave the reaction layer 8b including ChOD, ChE, the surface active agent, and CMC. The quantities of potassium ferricyanide, the surface active agent, ChOD, and ChE used in Example 2 as well as those in Examples 3 and 4 and Comparative Example discussed below were identical with those of Example 1.

The cholesterol sensor was then prepared in the same manner as discussed in Example 1. While the time period between a supply of the sample solution and application of a voltage is varied, the electric current was measured as the response with regard to each concentration of the sample solution. The results are shown in the graph of FIG. 4.

Example 3

Example 3 is a cholesterol sensor having the structure of FIG. 3, wherein the reaction layer 8b includes the electron mediator and the reaction layer 8a includes cholesterol oxidase, cholesterol esterase, and the surface active agent. This cholesterol sensor was prepared in the following manner.

The CMC layer 7 was formed on the electrode system upon the electrically insulating base plate 1 in the same manner as discussed in Example 1. The procedure of Example 3 prepared a mixed aqueous solution by dissolving ChOD, ChE, and the surface active agent in water, dropped 2.5 µl of the mixed aqueous solution on the CMC layer 7, froze the dropped solution with liquid nitrogen, and dried the frozen solution in a Kjeldahl flask set in the freeze-drying apparatus for 3 hours. This gave the reaction layer 8a including ChOD, ChE, and the surface active agent. The procedure, on the other hand, dissolved potassium ferricyanide in water to prepare an aqueous solution, dropped 1 µl of the aqueous solution in the recess defined by the slit 15 of the cover member including the cover and the spacer, froze the dropped solution with liquid nitrogen, and dried the frozen solution in a Kjeldahl flask set in the freeze-drying apparatus for 3 hours. This gave the reaction layer 8b including potassium ferricyanide.

The cholesterol sensor was then prepared in the same manner as discussed in Example 1. While the time period between a supply of the sample solution and application of a voltage is varied, the electric current was measured as the response with regard to each concentration of the sample solution. The results are shown in the graph of FIG. 4.

Example 4

Example 4 is a cholesterol sensor having the structure of FIG. 3, wherein the reaction layer 8a includes the electron mediator and the reaction layer 8b includes cholesterol oxidase, cholesterol esterase, and the surface active agent. This cholesterol sensor was prepared in the following manner.

The CMC layer 7 was formed on the electrode system upon the electrically insulating base plate 1 in the same manner as discussed in Example 1. The procedure of Example 4 dissolved potassium ferricyanide in water to prepare an aqueous solution, dropped 1 µl of the aqueous solution on the CMC layer 7, froze the dropped solution with liquid nitrogen, and dried the frozen solution in a Kjeldahl flask set in the freeze-drying apparatus for 3 hours. This gave the reaction layer 8a. The procedure, on the other hand, prepared a mixed aqueous solution by dissolving ChOD, ChE, and the surface active agent in water, dropped 2.5 µl of the mixed aqueous solution in the recess defined by the slit 15 of the cover member including the cover and the spacer, froze the dropped solution with liquid nitrogen, and dried the frozen solution in a Kjeldahl flask set in the freeze-drying apparatus for 3 hours. This gave the reaction layer 8b including ChOD, ChE, and the surface active agent.

The cholesterol sensor was then prepared in the same manner as discussed in Example 1. While the time period between a supply of the sample solution and application of a voltage is varied, the electric current was measured as the response with regard to each concentration of the sample solution. The results are shown in the graph of FIG. 4.

COMPARATIVE EXAMPLE

The CMC layer was formed on the electrode system upon the electrically insulating base plate 1 in the same manner as discussed in Example 1. A mixed aqueous solution was prepared by dissolving potassium ferricyanide, the surface active agent, ChOD, and ChE in water. The procedure of Comparative Example dropped 4.5 µl of the mixed aqueous solution on the CMC layer and dried the mixed aqueous solution with warm blast of 50° C. for 15 minutes. This gave a reaction layer including potassium ferricyanide, the surface active agent, ChOD, and ChE.

A cholesterol sensor was then prepared in the same manner as discussed in Example 1. While the time period between a supply of the sample solution and application of a voltage is varied, the electric current was measured as the response with regard to each concentration of the sample solution. The results are shown in the graph of FIG. 4.

The technique of the present invention forms a reaction layer having a large surface area. This arrangement ensures the rapid dissolution of the reaction layer in a sample solution and gives a resultant biosensor having excellent response to a substrate even in a high concentration range of the substrate.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. A method of manufacturing a biosensor which comprises an electrically insulating base plate, an electrode system including a measuring electrode and a counter electrode formed on the base plate, and a reaction reagent system including at least an oxidoreductase and an electron mediator as reagents, wherein the reagents of the reaction reagent system are present as a reaction layer structure that comprises at least one reaction layer, said method comprising a step of forming a specific reaction layer of the reaction layer structure, the specific layer comprising at least one of the reagents of the reaction reagent system, said step comprising:
(1) dissolving the at least one of the reagents in a solvent of a sublimable substance to prepare a solution;
(2) applying the solution on at least one of the base plate, the measuring electrode, and the counter electrode;
(3) freezing the applied solution; and
(4) sublimating the solvent included in a solid matter of the frozen solution under reduced pressure for removal, thereby forming the specific reaction layer on at least one of the base plate, the measuring electrode, and the counter electrode.

2. The method in accordance with claim 1, wherein the specific reaction layer contains all the reagents of the reaction reagent system.

3. The method in accordance with claim 1, wherein the reaction layer structure comprises a plurality of reaction layers and only the specific reaction layer contains the at least one reagent of the reaction reagent system.

4. The method in accordance with claim 3, wherein said oxidoreductase is an enzyme functioning as a catalyst of the oxidation reaction of cholesterol, and said electron mediator is contained in another reaction layer different from a reaction layer containing said enzyme.

5. The method in accordance with claim 3, wherein said oxidoreductase is an enzyme functioning as a catalyst of the oxidation reaction of cholesterol, and the layer containing said enzyme further contains a surface active agent.

6. The method in accordance with claim 3, wherein said at least one reagent of the reaction reagent system is the oxidoreductase.

7. The method in accordance with claim 3, wherein said at least one reagent of the reaction reagent system consists of said oxidoreductase and a surface active agent.

8. The method in accordance with claim 3, wherein said at least one reagent of the reaction reagent system is the electron mediator.

9. The method in accordance with claim 8, wherein the electron mediator is potassium ferricyanide.

10. The method in accordance with claim 1, wherein at least a lower-most reaction layer of the reaction layer structure includes a hydrophilic polymer.

11. A The method in accordance with claim 1, wherein said electron mediator is potassium ferricyanide.

12. A biosensor manufactured by the method of claim 1.

13. A method of manufacturing a biosensor which comprises an electrically insulating base plate, an electrode system including a measuring electrode and a counter electrode formed on said base plate, and a reaction reagent system including as reagents at least an oxidoreductase and an electron mediator, wherein the reagents of said reaction reagent system are included in a reaction layer structure comprising one or more reaction layers, and further wherein at least one of the reagents of said reaction reagent system is contained only in an upper-most layer of a specific reaction layer comprising a stack of layers, said method comprising a step of forming said specific reaction layer, said step comprising:
pre-forming the stack of layers on at least one of the base plate, the measuring electrode, and the counter electrode without the upper-most layer;
dissolving the at least one reagent in a solvent of a sublimable substance to prepare a solution;
applying the solution on the pre-formed stack of layers without the upper-most layer;
freezing the applied solution; and
sublimating the solvent included in a solid matter of the frozen solution under reduced pressure for removal.

14. A method of manufacturing a biosensor which comprises an electrically insulating base plate, an electrode system comprising a measuring electrode and a counter electrode, the system being formed on the base plate, a reaction reagent system comprising at least an oxidoreductase and an electron mediator, wherein the reagents are present as a reaction layer structure comprising at least one reaction layer, and a cover member being joined with the base plate to define a sample solution supply pathway, whereby a sample solution flows to the electrode system through the sample solution supply pathway, the reaction layer structure being exposed to the sample solution supply pathway, said method comprising a step of forming a specific reaction layer of the reaction layer structure, the specific layer comprising at least one of the reagents of the reaction reagent system, said step comprising:
(1) dissolving the at least one of the reagents in a solvent of a sublimable substance to prepare a solution;
(2) applying the solution on the cover member;
(3) freezing the applied solution; and
(4) sublimating the solvent included in a solid matter of the frozen solution under reduced pressure for removal, thereby forming the specific reaction layer on the cover member.

15. A method of manufacturing a biosensor which comprises an electrically insulating base plate, an electrode system including a measuring electrode and a counter electrode formed on said base plate, a cover member which is joined with the base plate to define a sample solution supply pathway, and a reaction reagent system including as reagents at least an oxidoreductase and an electron mediator, wherein the reagents of said reaction reagent system are included in a reaction layer structure comprising one or more reaction layers formed on the cover member, whereby the reaction layer structure is exposed to the sample solution supply pathway, and further wherein at least one of the reagents of said reaction reagent system is contained only in an upper-most layer of a specific reaction layer comprising a stack of layers, said method comprising a step of forming said specific reaction layer, said step comprising:
pre-forming the stack of layers on the cover member without the upper most layer;
dissolving the at least one reagent in a solvent of a sublimable substance to prepare a solution;
applying the solution on the pre-formed stack of layers without the upper-most layer;
freezing the applied solution; and
sublimating the solvent included in a solid matter of the frozen solution under reduced pressure for removal.

* * * * *